US 6,530,880 B2

(12) United States Patent
Pagliuca

(10) Patent No.: US 6,530,880 B2
(45) Date of Patent: Mar. 11, 2003

(54) APPARATUS FOR SUPPORTING AN ENDOSCOPE

(75) Inventor: James J. Pagliuca, Millis, MA (US)

(73) Assignee: Endius Incorporated, Plainville, MA (US)

( * ) Notice: Subject to any disclaimer, the term of this patent is extended or adjusted under 35 U.S.C. 154(b) by 173 days.

(21) Appl. No.: 09/821,297

(22) Filed: Mar. 29, 2001

(65) Prior Publication Data

US 2002/0143235 A1 Oct. 3, 2002

(51) Int. Cl.⁷ ................................................ A61B 1/00
(52) U.S. Cl. ....................................... 600/102; 600/114
(58) Field of Search ................................ 600/102, 114; 606/130

(56) References Cited

U.S. PATENT DOCUMENTS

| | | | |
|---|---|---|---|
| 3,044,461 A | | 7/1962 | Murdock |
| 4,863,133 A | | 9/1989 | Bonnell |
| 4,899,729 A | | 2/1990 | Gill et al. |
| 5,163,949 A | | 11/1992 | Bonutti |
| 5,197,971 A | | 3/1993 | Bonutti |
| 5,224,680 A | * | 7/1993 | Greenstein et al. ......... 600/102 |
| 5,354,302 A | | 10/1994 | Ko |
| 5,520,607 A | | 5/1996 | Frassica et al. |
| 5,571,072 A | | 11/1996 | Konner |
| 5,575,754 A | * | 11/1996 | Konomura ............... 600/114 X |
| 5,707,359 A | | 1/1998 | Bufalini |
| 5,792,044 A | | 8/1998 | Foley et al. |
| 5,902,231 A | | 5/1999 | Foley et al. |
| 6,187,000 B1 | | 2/2001 | Davison et al. |
| 6,361,488 B1 | * | 3/2002 | Davison et al. ............. 600/102 |

OTHER PUBLICATIONS

MicroEndoscopic Discectomy System, dated 1997, MED™ presentation materials (33 pages).
Spine Endoscopy System with Flexposure dated 1999, Endius™ presentation materials (2 pages).
Method For Performing a Surgical Procedure And a Cannula For Use In Performing The The Surgical Procedure U.S. Ser. No. 09/772,605, filed Jan. 30, 2001.
Support Apparatus For Endoscopic Surgery, U.S. Ser. No. 09/491,808, filed Jan. 28, 2000.

* cited by examiner

Primary Examiner—Kevin Lee
(74) Attorney, Agent, or Firm—Tarolli, Sundheim, Covell & Tummino L.L.P.

(57) ABSTRACT

An apparatus (10) supports an endoscope (200) for viewing a surgical site in a patient during surgery on the patient. The apparatus (10) includes a base (118), a part (140) adapted to be fixed to the endoscope (200), and a screw mechanism (160). The base (118) has a guide portion (128). The part (140) engages the guide portion (128) and is movable relative to the guide portion (128). The screw mechanism (160) connects between the base (118) and the part (140). At least a portion (610) of the screw mechanism (160) is rotatable to slide the part (140) relative to the guide portion (128) to change a position of the endoscope (200) relative to the patient. In another feature of the apparatus (10), the apparatus (10) may include a cannula clamp 180 secured to a cannula (11) and rotatable relative to the part (140).

42 Claims, 9 Drawing Sheets

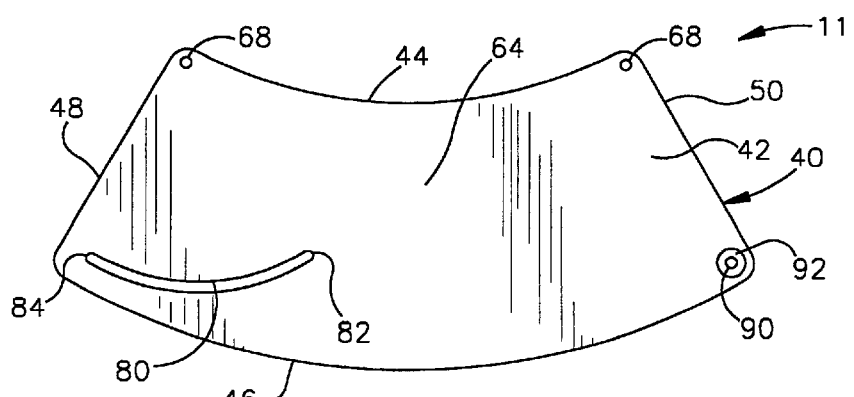
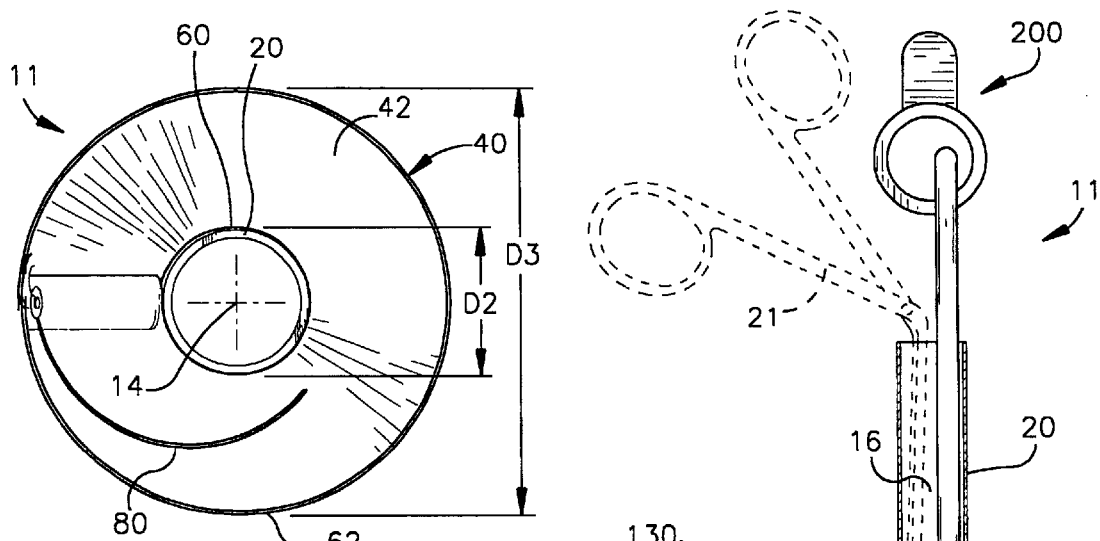
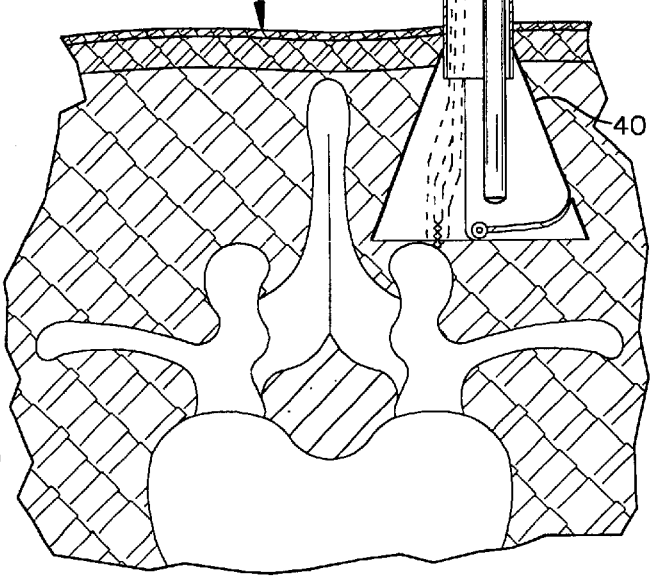
Fig.4
Fig.3
Fig.5

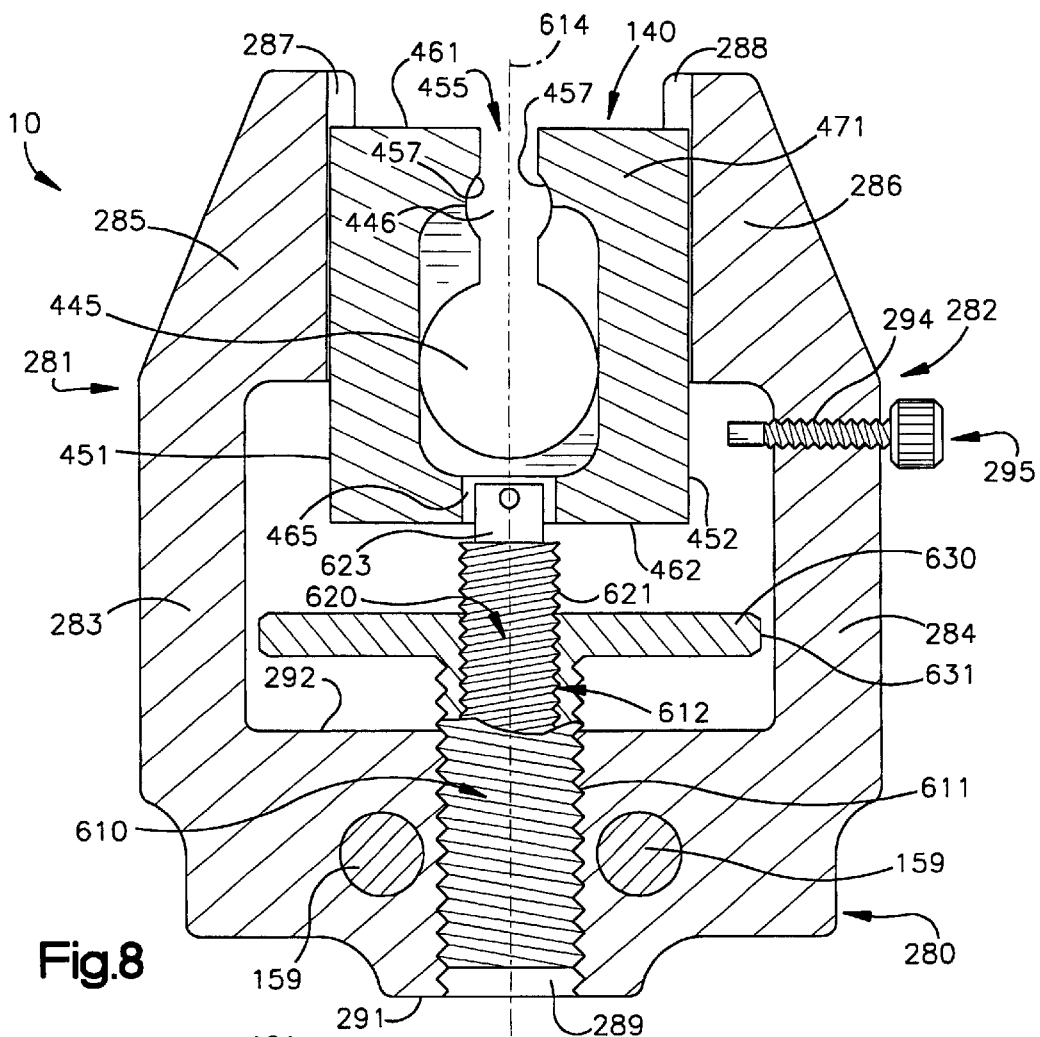
Fig.8
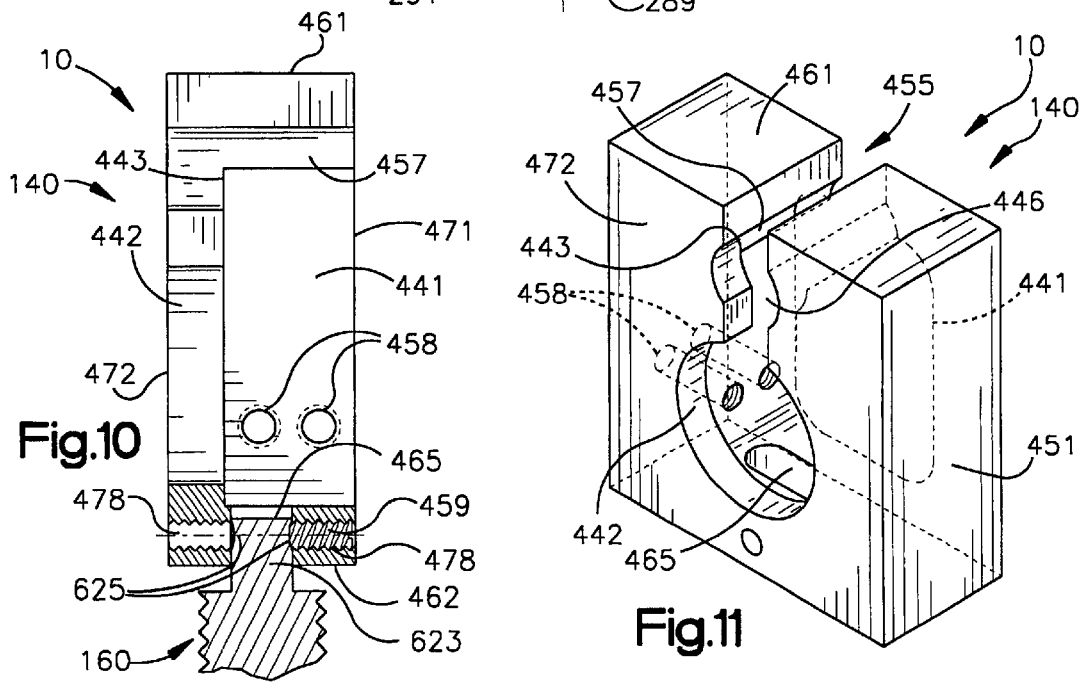
Fig.10
Fig.11

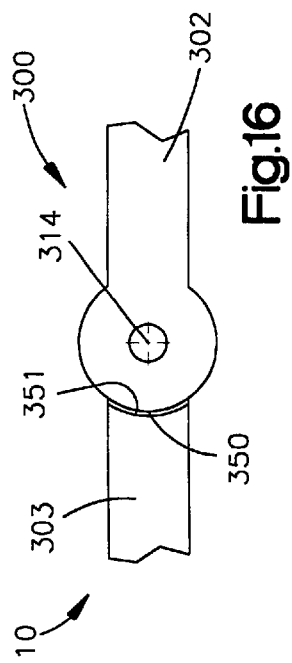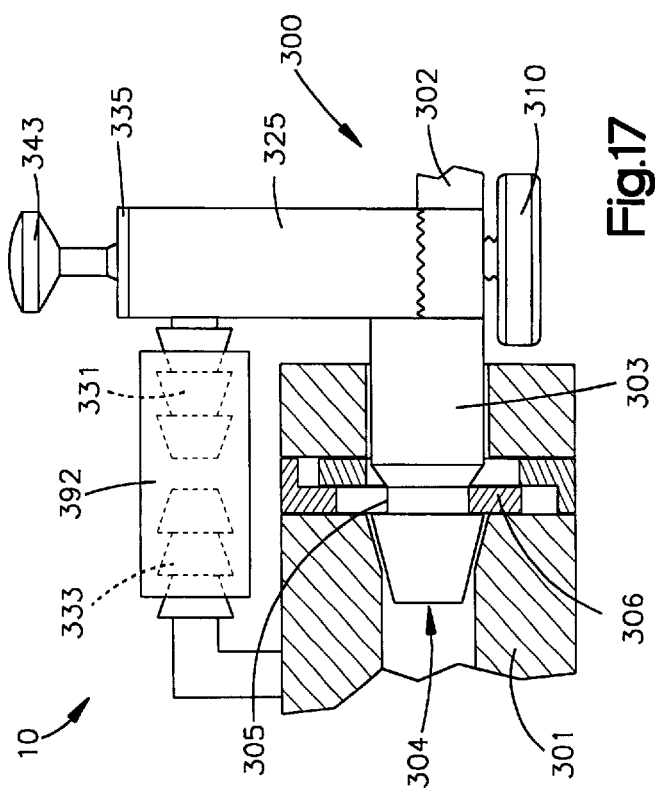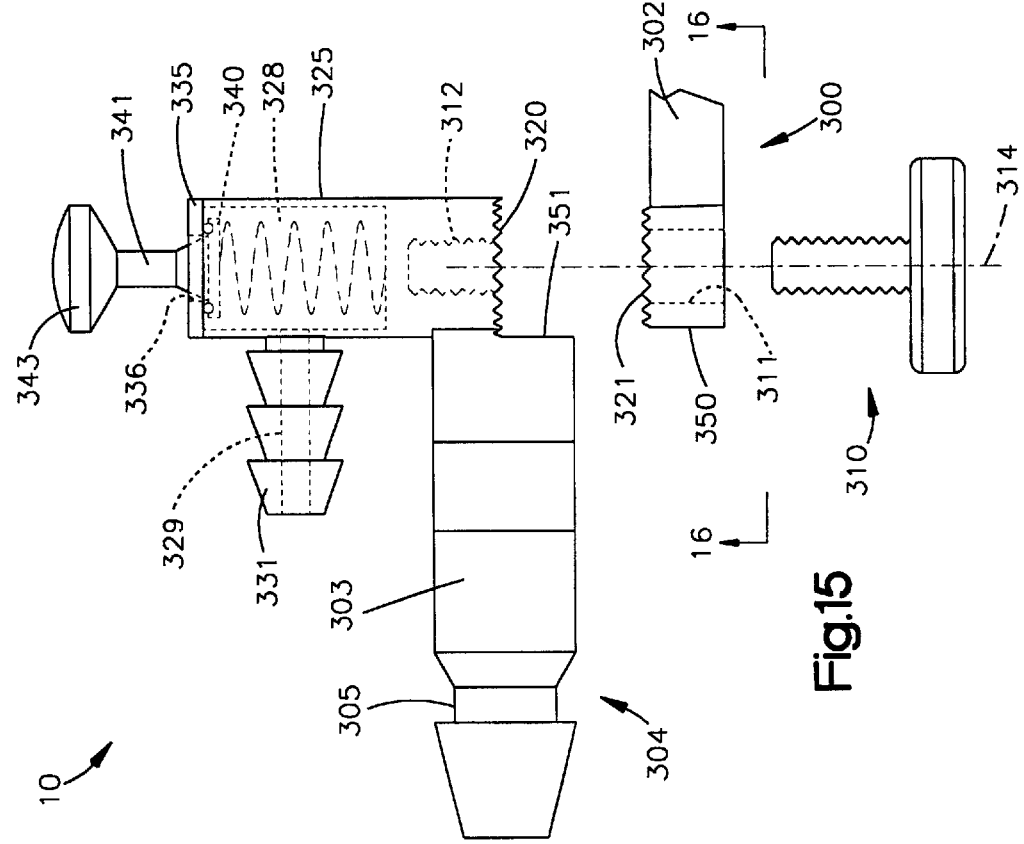

APPARATUS FOR SUPPORTING AN ENDOSCOPE

TECHNICAL FIELD

The present invention relates to an apparatus for supporting an endoscope and, more particularly, for supporting an endoscope for viewing a surgical site in a patient during surgery on the patient.

BACKGROUND OF THE INVENTION

Percutaneous surgery is a procedure in which surgical instruments, and typically an endoscope, are inserted through a cannula into the body of a patient. A viewing element, typically a small video camera, is part of the endoscope and is connected to a television monitor so that the surgeon may view the surgical site.

The cannula is a hollow tube. The cannula is inserted through an incision into the body of a patient. The instruments and the endoscope are inserted through the cannula. The cannula also allows the instruments and endoscope to be removed from the body and/or adjusted in the body during the surgery.

A conventional apparatus for supporting the endoscope allows a surgeon to manipulate the surgical instruments without also moving the endoscope. Also, a known support apparatus allows adjustment of the endoscope relative to the cannula for viewing different areas at the surgical site.

SUMMARY OF THE INVENTION

In accordance with one feature of the present invention, an apparatus supports an endoscope for viewing a surgical site in a patient during surgery on the patient. The apparatus includes a base, a part adapted to be fixed to the endoscope, and a screw mechanism. The base has a guide portion. The part engages the guide portion and is movable relative to the guide portion. The screw mechanism connects the base and the part. At least a portion of the screw mechanism is rotatable to slide the part relative to the guide portion to change a position of the endoscope relative to the patient.

In accordance with another feature of the present invention, an apparatus supports an endoscope for viewing a surgical site in a patient during surgery on the patient. The endoscope extends through a cannula into the patient. The apparatus includes a base, a support mechanism for supporting the endoscope on the base, a cannula clamp, and a connection between the base and the cannula clamp. The cannula clamp clamps against an outer surface of the cannula. The connection enables the base to rotate relative to the cannula clamp about an axis of the cannula. The connection includes an index mechanism with parts interposed between the base and the cannula clamp for retaining the base at incremental relatively rotated positions relative to the cannula clamp.

In accordance with still another feature of the present invention, an apparatus supports an endoscope for viewing a surgical site in a patient during surgery on the patient. The endoscope extends through a cannula into the patient. The apparatus includes a base and a cannula clamp. The base supports the endoscope. The cannula clamp includes a pair of arms for clamping against an outer surface of the cannula through which the endoscope extends. The apparatus includes an actuator for moving the arms a predetermined distance toward each other to effect clamping against the cannula. The cannula clamp further includes an adjustment mechanism for changing the relative position of the arms from which the arms are moved by the actuator to enable the arms to clamp different diameter cannulas.

In accordance with yet another feature of the present invention, an apparatus supports an endoscope for viewing a surgical site in a patient during surgery on the patient. The apparatus includes a part for engaging the endoscope. The part has a first surface portion for engaging an external surface of the endoscope and a second surface portion spaced apart from the first surface portion for engaging an outer surface of the endoscope defining a light port.

In accordance with still another feature of the present invention, an apparatus supports an endoscope for viewing a surgical site in a patient during surgery on the patient. The apparatus includes a base, a first part, a second part, and a mechanism for enabling axial and rotational adjustment of the first part relative to the second part. The base is for supporting the endoscope. The first part is adapted to be fixed to the endoscope. The second part is adapted to be fixed to a cannula with a longitudinal axis. The mechanism includes a member supported on the base for rotation relative to the base about an axis parallel to the longitudinal axis of the cannula and spaced apart from the longitudinal axis of the cannula.

In accordance with yet another feature of the present invention, an apparatus supports an endoscope for viewing a surgical site in a patient during surgery on the patient. The apparatus includes a cannula for insertion into the patient, a cannula clamp, a base, and a part supported for linear movement on the base relative to the base. The cannula clamp engages an outer surface of the cannula. The base is supported for rotation relative to the cannula clamp about a longitudinal axis of the cannula. The part is adapted to be fixed to the endoscope. The part moves in a path parallel to the longitudinal axis of the cannula.

BRIEF DESCRIPTION OF THE DRAWINGS

The foregoing and other features of the present invention will become more apparent to one skilled in the art upon consideration of the following description of the invention and the accompanying drawings, in which:

FIG. 3 is a schematic end view showing the cannula of FIG. 1 in the expanded position;

FIG. 4 is a rollout view of a part of the cannula of FIG. 1;

FIG. 5 is a schematic sectional view of the cannula of FIG. 1 during a surgical procedure.

FIG. 8 is a schematic sectional view taken along line 8—8 in FIG. 7;

FIG. 9 is a schematic sectional view taken along line 9—9 in FIG. 7;

FIG. 10 is a schematic view partially in section of part of the apparatus of FIG. 6;

FIG. 11 is a schematic perspective view of a portion of FIG. 10;

FIG. 15 is an exploded schematic view of part of the apparatus of FIG. 6;

FIG. 16 is a schematic view taken along line 16—16 in FIG. 15;

FIG. 17 is a schematic view showing the parts of FIG. 15 with an associated mechanical arm.

DESCRIPTION OF A PREFERRED EMBODIMENT

Figure 2:
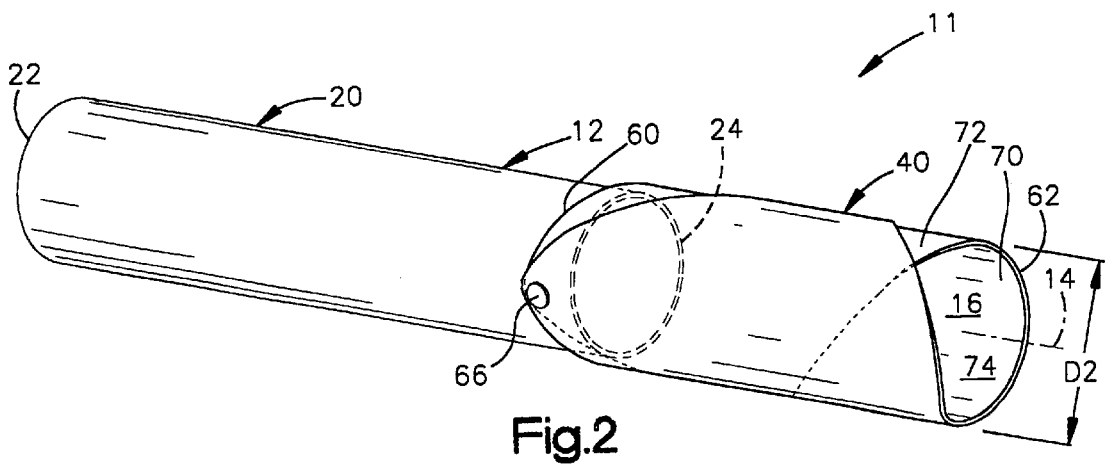
FIG. 2 is a perspective view of the cannula of FIG. 1 with parts removed for clarity, the cannula being shown in a contracted condition.

As representative of the present invention, the Figures illustrate an apparatus 10 (FIG. 6) for use in percutaneous surgery in association with a cannula 11 (FIG. 2). The apparatus 10 includes a base 118, a part 140 adapted to be fixed to an endoscope 200, a screw mechanism 160 connected between the base and the part, and a cannula clamp 180 connected with the base. The cannula clamp 180 may form a second part of the apparatus 10 that is adapted to be fixed to the cannula 11. The part 140 and endoscope 200 are rotatable relative to the cannula clamp 180.

A conventional cannula is a cylindrical metal or plastic tube with a channel extending completely through the cannula. The channel has a central axis. The cannula is inserted through an incision into a body of a patient during surgery.

FIGS. 1–5 illustrate one suitable cannula 11 constructed for use with an apparatus 10 in accordance with the present invention. U.S. patent application Ser. No. 09/772,605, filed Jan. 30, 2001 in the names of Thomas Davison et al., discloses other cannula structures that may be used with the apparatus 10. A specific cannula structure is not envisioned as part of the present invention. The cannula 11 will be described below by way of example of a cannula usable with the present invention.

The cannula 11 (FIGS. 1–5) is a tubular structure 12 centered on a central axis 14. The tubular structure 12 defines a passage 16 through the cannula 11. Surgical instruments and an endoscope are inserted into a patient's body through the passage 16 during surgery.

The tubular structure 12 comprises a first tubular portion 20 and a second tubular portion 40 attached to the first tubular portion. The first tubular portion 20 is preferably made of a length of stainless steel tubing, but could alternatively be made of another suitable material. The first tubular portion 20 has a proximal end 22 and a distal end 24. Parallel cylindrical inner and outer surfaces 26 and 28, respectively, extend between the ends 22, 24 of the first tubular portion 20. The inner surface 26 defines a first passage portion 30 of the passage 16 through the cannula 11. The first passage portion 30 has a diameter D1 that is preferably in the range from 10 mm to 30 mm.

The second tubular portion 40 of the tubular structure 12 is attached to the distal end 24 of the first tubular portion 20. The second tubular portion 40 is preferably made from stainless steel, but could alternatively be made from another suitable material.

As best seen in the rollout view of FIG. 4, the second tubular portion 40 comprises an arcuate segment 42 of sheet stock. The arcuate segment 42 includes first and second arcuate edges 44 and 46, respectively, and first and second planar edges 48 and 50, respectively. The first and second planar edges 48 and 50 are rolled in an overlapping manner to form the tubular configuration of the second tubular portion 40.

When the second tubular portion 40 has been rolled into its tubular configuration, the first and second arcuate edges 44 and 46 define oppositely disposed first and second ends 60 and 62 (FIGS. 1 and 2), respectively, of the second tubular portion. The first and second ends 60 and 62 are connected by a central portion 64. The first end 60 of the second tubular portion 40 is attached to the distal end 24 of the first tubular portion 20 by a single fastener, such as a rivet 66. The rivet 66 extends through two aligned apertures 68 (FIG. 4) at the first end 60 of the second tubular portion 40. The first end 60 of the second tubular portion 40 is pivotable about the rivet 66.

The second tubular portion 40 includes parallel inner and outer surfaces 70 and 72 (FIGS. 1 and 2), respectively, extending between the first and second ends 60 and 62. The inner surface 70 defines a second passage portion 74 of the passage 16 through the cannula 11 that extends as a continuation of the first passage portion 30 in the first tubular portion 20.

An arcuate slot 80 is formed in the second tubular portion 40 and extends between the inner and outer surfaces 70 and 72 of the second tubular portion. The arcuate slot 80 extends along a curvilinear path in the central portion 64 of the second tubular portion 40 toward the second end 60 of the second tubular portion. The arcuate slot 80 has a first terminal end 82 located in the central portion 64 of the second tubular portion 40. A second terminal end 84 of the arcuate slot 80 is located adjacent the intersection of the second arcuate edge 46 and the first planar edge 48 of the arcuate segment 42.

A guide pin 90 is attached to the inner surface 70 of the second tubular portion 40 adjacent the intersection of the second arcuate edge 46 and the second planar edge 50. In the tubular configuration of the second tubular portion 40, the guide pin 90 is located in the arcuate slot 80 and is movable along the curvilinear path of the arcuate slot. A washer 92 is secured to an inner end of the guide pin 90 to retain the guide pin in the arcuate slot 80.

Figure 1:
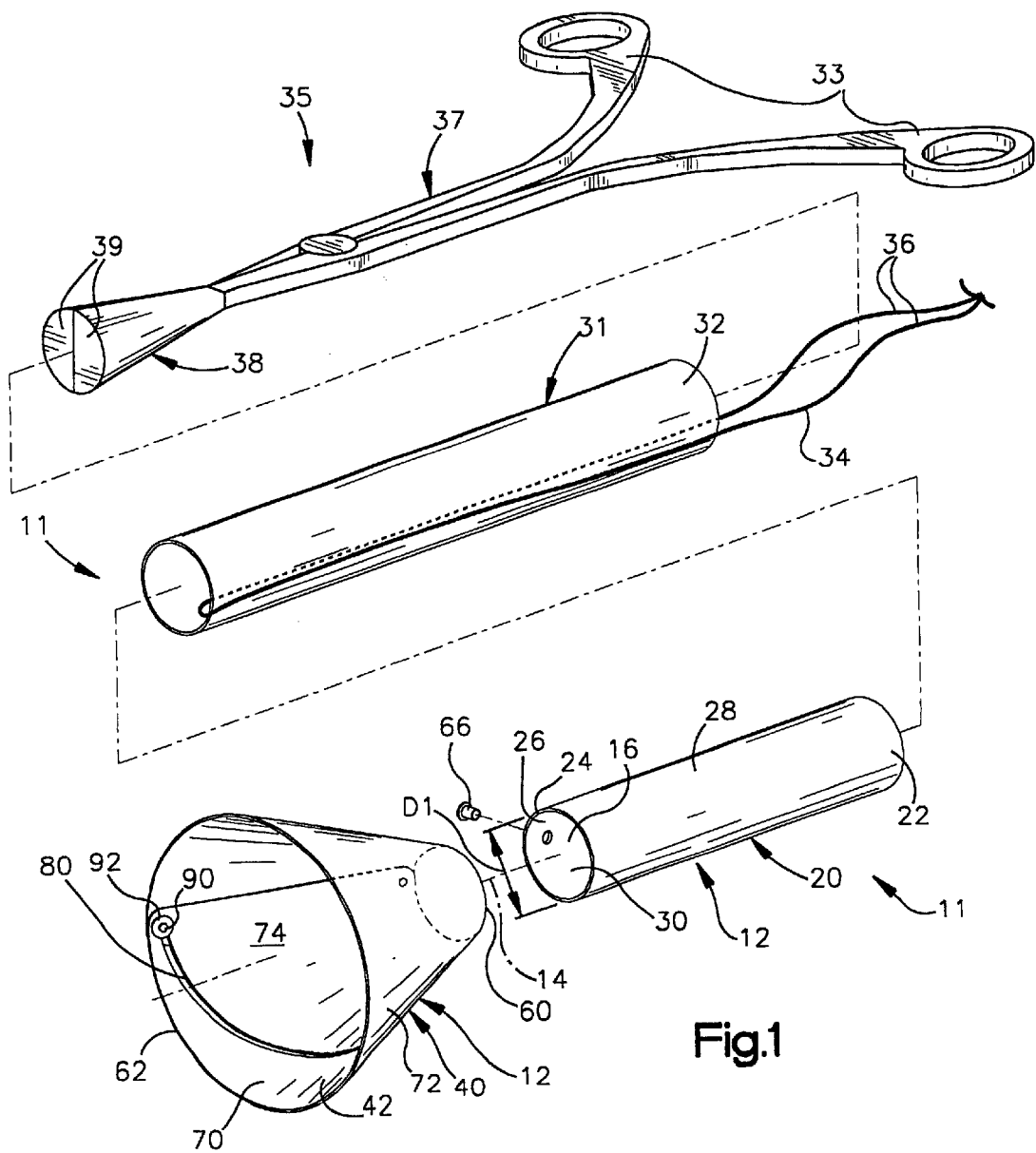
FIG. 1 is an exploded schematic view illustrating an expandable cannula constructed for use with the present invention.

The second tubular portion 40 of the tubular structure 12 is expandable from a contracted condition shown in FIG. 2 to an expanded condition shown in FIG. 1. In the contracted condition, the guide pin 90 is located in the first terminal end 82 of the arcuate slot 80 in the second tubular portion 40 and the second passage portion 74 defined by the second tubular portion is cylindrical in shape. The second passage 74 has a generally constant diameter D2 (FIGS. 2 and 3) that is approximately equal to the diameter D1 of the first tubular portion 20. Thus, the cross-sectional area of the second passage portion 74 at the second end 62 of the second tubular portion 40, which is a function of the diameter D2, is approximately the same as the cross-sectional area at the first end 60 of the second tubular portion and is approximately the same as the cross-sectional area of the first passage portion 30 in the first tubular portion 20.

In the expanded condition, the guide pin 90 is located in the second terminal end 84 of the arcuate slot 80 in the second tubular portion 40 and the second tubular portion has a frustoconical configuration. At the second end 62 of the second tubular portion 40, the second passage portion 74 has a diameter D3 (FIG. 3) that is larger then the diameter D2 of the second passage portion at the first end 60. Preferably, the diameter D3 of the second passage portion 74 at the second end 62 of the second tubular portion is 40% to 80% greater than the diameter D1 of the second passage portion at the first end 60.

Thus, in the expanded condition, the cross-sectional area of the second passage portion 74 at the second end 62 of the second tubular portion 40, which is a function of the diameter D3, is 16% to 64% greater than the cross-sectional area of the second passage portion at the first end 60 of the second tubular portion. In the expanded condition, the cross-sectional area of the second passage portion 74 at the second end 62 of the second tubular portion 40 may be large enough to overlie a major portion of at least two adjacent vertebrae of a patient.

The cannula 11 includes an outer layer 31 (FIG. 1) for maintaining the second tubular portion 40 of the cannula 11 in the contracted condition. It is contemplated that other suitable means for maintaining the second tubular portion 40 in the contracted condition could be employed. The outer layer 31 comprises a section of plastic tubing 32 which is heat shrunk over both the first and second tubular portions 20, 40 to hold the second tubular portion in the contracted condition.

In addition, a loop of polyester string 34 for tearing the heat shrunk tubing 32 is wrapped around the heat shrunk tubing so that it extends both underneath and on top of the tubing. An outer end 36 of the string 34 extends beyond the tubing 32.

FIG. 1 shows an actuatable device 35 for expanding the second tubular portion 40 from the contracted condition to the expanded condition. The actuatable device 35 comprises a manually operated expansion tool 37. The expansion tool 37 resembles a common pair of scissors and has a pair of legs 33 pivotally connected to one another. The expansion tool 37 includes a frustoconical end section 38 formed by a pair of frustoconical halves 39. Each of the frustoconical halves 39 extends from a respective one of the legs 33 of the expansion tool 37. It is contemplated that other suitable means for expanding the second tubular portion 40 toward the expanded condition could be employed, such as an inflatable balloon (not shown).

During an endoscopic surgical procedure, the cannula 11 is inserted into the body of a patient in the contracted condition. The outer end 36 of the string 34 is then manually pulled on by the surgeon. Pulling on the string 34 tears the heat shrunk tubing 32 most of the way along the heat shrunk tubing, which frees the second tubular portion 40 for expansion. The heat shrunk tubing 32, in its torn condition, may remain attached to the first tubular portion 20.

Next, the expansion tool 37 is inserted into the passage 16 in the cannula 11 until the frustoconical end section 33 is located at the second end 62 of the second tubular portion 40. The legs 33 of the expansion tool 37 are manually separated, causing the frustoconical halves 39 to separate also. As the halves 39 separate, a radially outward directed force is exerted on the inner surface 70 of the second tubular portion 40 by the halves 39, causing the second tubular portion to expand toward the expanded condition. Under the force of the expanding expansion tool 37, the guide pin 90 slides from the first terminal end 82 of the arcuate slot 80 to the second terminal end 84 of the arcuate slot to permit the expansion of the second tubular portion 40. The expansion tool 37 can be rotated about the central axis 14 to ensure that the second tubular portion 40 of the cannula 11 is completely expanded to the expanded condition. The expansion tool 37 is then collapsed and removed so that one or more surgical instruments (indicated schematically at 21 in FIG. 5) and a viewing element (indicated schematically as part of the endoscope 200 in FIG. 5) can be received through the cannula 11 and inserted into a patient's body 130. The expanded second tubular portion 40 of the cannula 11 provides a large working area for the surgeon inside the body 130.

The expanded tubular portion 40 can dilate and locally retract and separate spinalis muscle and soft tissues from the vertebrae thereby creating an endoscopic operating field at the surgical site. This endoscopic operating field within the spinal muscles differs from arthroscopic, laparoscopic, or cystoscopic working spaces in that there is no physiologic space or defined tissue plane that is insufflated with air or distended with fluid.

Figure 6:
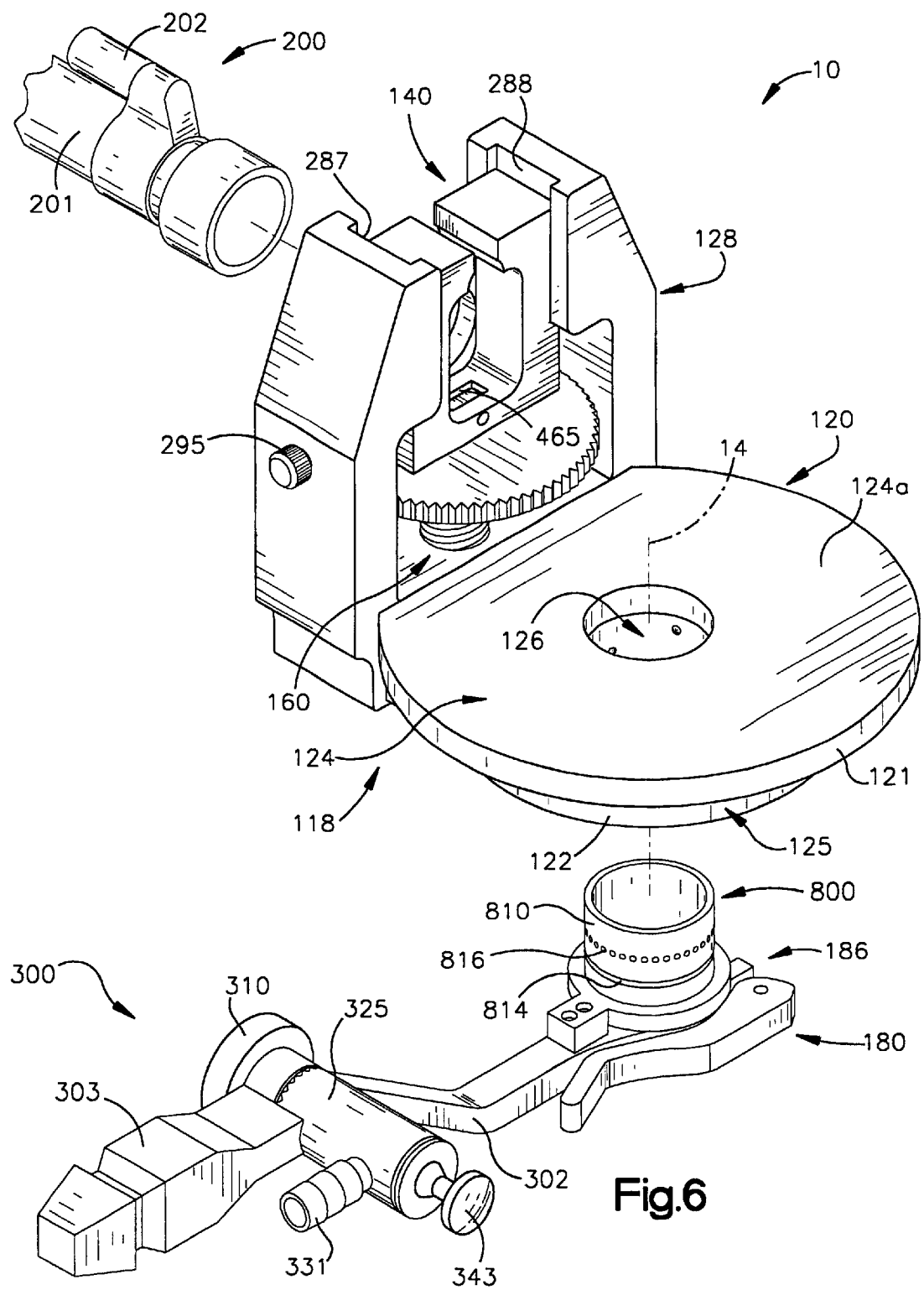
FIG. 6 is an exploded perspective view of an apparatus constructed in accordance with the present invention.
Figure 7:
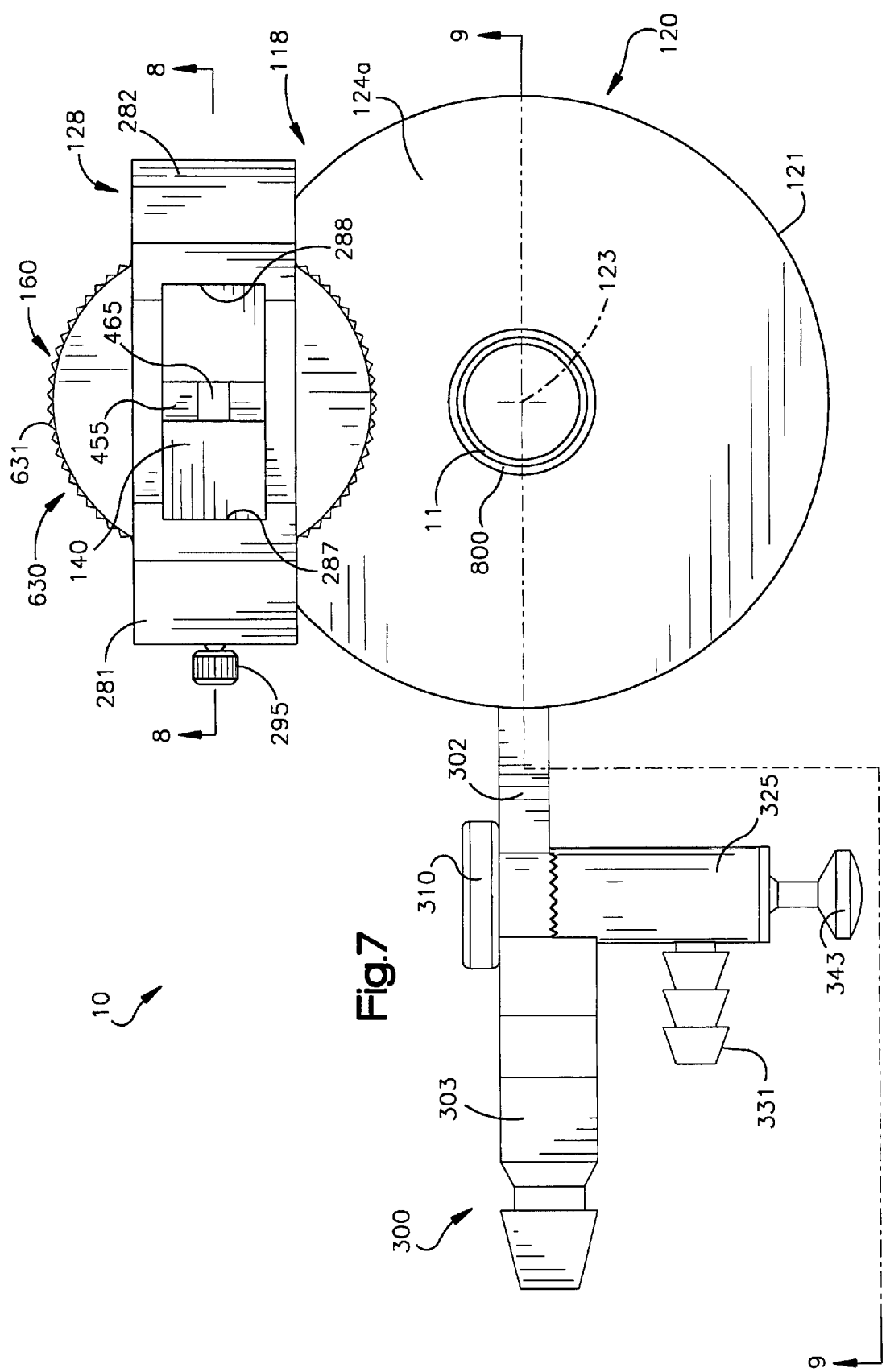
FIG. 7 is a schematic top view of the apparatus of FIG. 6.
Figure 13:
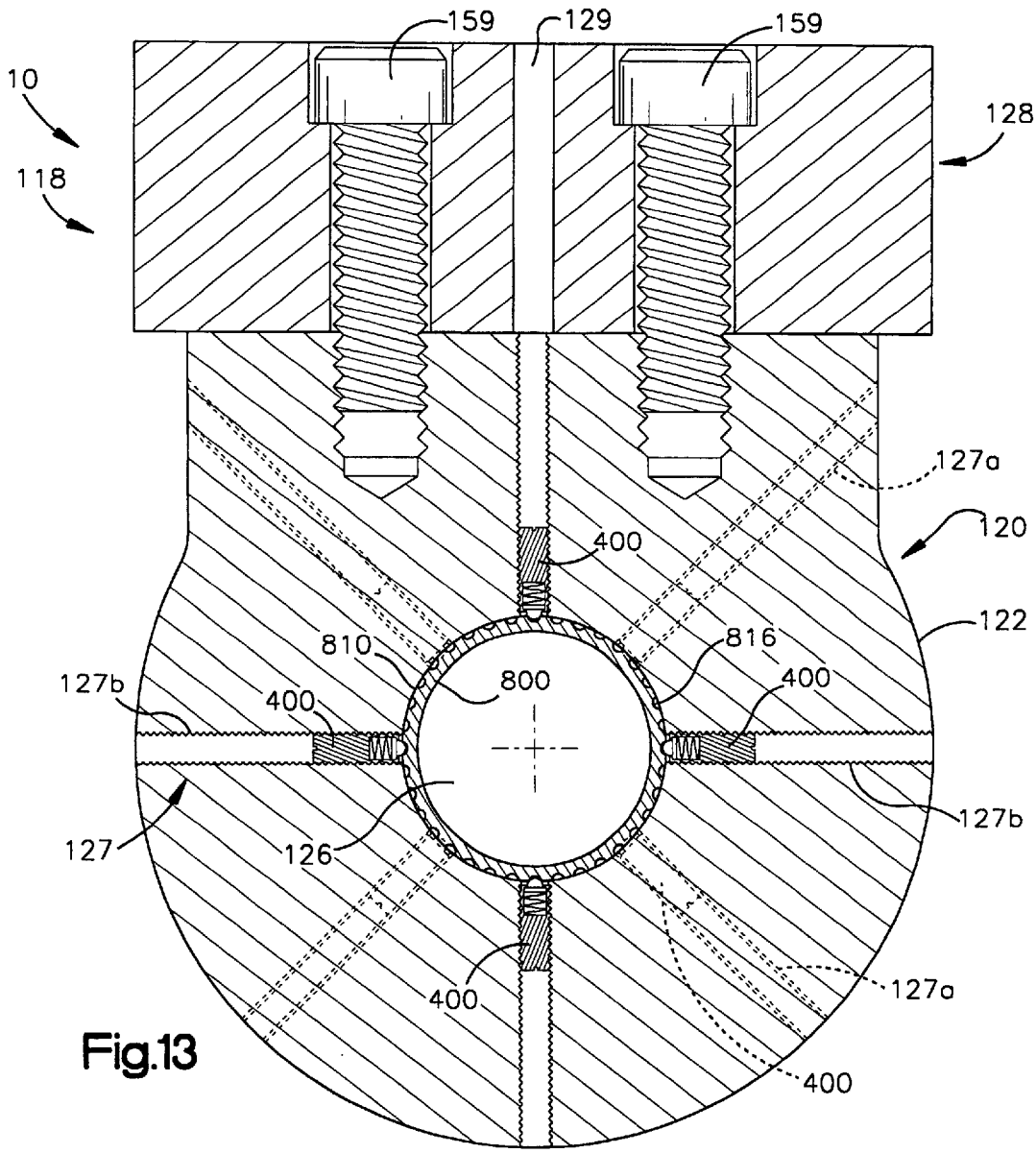
FIG. 13 is a schematic sectional view taken along line 13—13 in FIG. 9.

As viewed in FIG. 6, the apparatus 10 of the present invention may be associated with the cannula 11 of FIGS. 1–5. The apparatus 10 includes the base 118. The base 118 includes a base portion 120 and a guide portion 128. The base portion 120 is secured to the guide portion 128 by conventional threaded fasteners 159 (FIG. 13).

The base portion 120 comprises a first generally cylindrical platform, or first disk 124, and a second generally cylindrical understructure, or second disk 125. The first disk 124 has an upper circular surface area 124a. The first disk 124 has a first circular perimeter 121, and the second disk 125 has a second smaller circular perimeter 122. A central, circular aperture 126 in the central area of the first and second disks 124, 125 extends through the disks. The first and second perimeters 121, 122 have a center 123 located at the center of the central aperture 126.

A cylindrical sleeve part 800 is secured to the cannula clamp 180 by conventional fasteners 290 (FIG. 9) and is located in the central aperture 126. The proximal end 22 of the cannula 11 can be easily inserted into, and removed from, the sleeve part 800. When the cannula 11 is located in the sleeve part 800, an axis of the sleeve part extends through the center of the central aperture 126 and the axis of the cannula also extends through the center of the central aperture 126. Thus, the cannula 11 and the sleeve part 800 are concentric about the central axis 14.

As viewed in FIG. 8, the guide portion 128 of the base 118 includes a horizontal base part 280, a first upright member 281 extending upward from the base part, and a second upright member 282 extending upward from the base part. The upright members 281, 282 have respective lower portions 283, 284 extending upward and parallel to each other. The upright members 281, 282 further have respective upper portions 285, 286 extending upward from the lower portions 283, 284 and toward each other. Each upper portion 285, 286 has a respective vertical, linear track 287, 288 for slidingly receiving the part 140.

The base part 280 has a right-hand threaded bore 289 extending vertically from a lower surface 291 of the base part to an upper surface 292 of the base part. The upper surface 292 is located between the upright members 281, 282.

One of the upright members 281, 282 may have a horizontal threaded bore 294 for receiving a stop member 295. The stop member 295 has a partially threaded shaft with a non-threaded end that extends horizontally through the upright member 281 or 282 into the area between the upright members 281, 282. The non-threaded end acts as a vertical limit stop for a part 630 of the screw mechanism 160.

As viewed in FIG. 6, the part 140 connects to the endoscope 200. The endoscope 200 consists of an endoscopic camera 201 and a light port 202. Part of the endoscope 200 (FIG. 5) may extend through the channel 12 of the cannula 11 into the patient's body.

The part 140 comprises a generally rectangular body having a passage through which the endoscope 200 extends. As viewed in FIGS. 10 and 11, the part 140 includes six planar sides. These sides define first and second opposite, generally rectangular guide surfaces 451, 452 (FIG. 8), first and second opposite, generally rectangular engagement surfaces 461, 462 (FIG. 10), and first and second opposite, generally square lateral surfaces 471, 472.

The passage in the part 140, through which the endoscope 200 extends, includes a first generally rectangular passage portion 441 and a second passage portion 442 sized for receiving the endoscopic camera 201. A transition point 443 in the passage is located where the first passage portion 441 and the second passage portion 442 come together.

The first passage portion 441 extends horizontally from the first lateral surface 471 through about ⅔ of the distance between the lateral surfaces 471, 472 to the transition point 443. The second passage portion 442 includes a cylindrical passage portion that communicates with the first passage portion 441 and extends horizontally from the transition point 443 to the second lateral surface 472. The second passage portion 442 forms a circular opening 445 in the lateral surface 472. The perimeter of the circular opening 445 forms a surface for tightly engaging the endoscopic camera 201 of the endoscope 200.

The part 140 further includes a slot 455 for receiving the light port 202 of the endoscope 200 and, an electric cord (not shown) of the endoscope 200. The slot 455 extends vertically upward from the first and second passage portions 441, 442 that receive the endoscopic camera 201. The slot 455 intersects the first engagement surface 461. The slot 455 extends horizontally from the first lateral surface 471 to the second lateral surface 472 and intersects the lateral surfaces. The portion of the slot 455 that is adjacent the first passage portion 441 is defined by curved edges 457 for abuttingly engaging the light port 202.

The slot 455 further includes a cylindrical portion 446 (FIG. 8). The cylindrical portion 446 has a surface that is sized to tightly engage the light port 202. The cylindrical portion 446 intersects the second lateral surface 472 and forms a circular opening in the second lateral surface. The cylindrical portion 446 has a smaller diameter than the first circular opening 445. The curved edges 457 of the slot 455 extend a part of the circle defined by the cylindrical portion 446 from the transition point 443 to the first lateral surface 471.

The second engagement surface 462 of the part 140 includes a generally rectangular slot 465 for receiving a part 623 (FIG. 10) of the screw mechanism 160. The slot 465 extends vertically upward from the second engagement surface 462 to the first passage portion 441. The slot 465 may have rounded ends, as viewed in FIG. 11.

One of the guide surfaces 451, 452 may have one or two threaded bores 458 extending horizontally from the guide surfaces 451, 452 to the first passage portion 441. These bores 458 may have set screws 459, such as conventional threaded fasteners, or ball plungers 400 (discussed below), threaded into them for engaging and releasably securing the endoscope 200 to the part 140.

Each lateral surface 471, 472 has a threaded bore 478 penetrating from the guide surface 471, 472 to the slot 465. These bores 478 may have set screws or ball plungers 400 threaded into them for releasably securing the part 623 of the screw mechanism 160 in the slot 465. A ball plunger 400 is illustrated in FIG. 10 releasably securing the part 623 in the slot 465.

Figure 14:
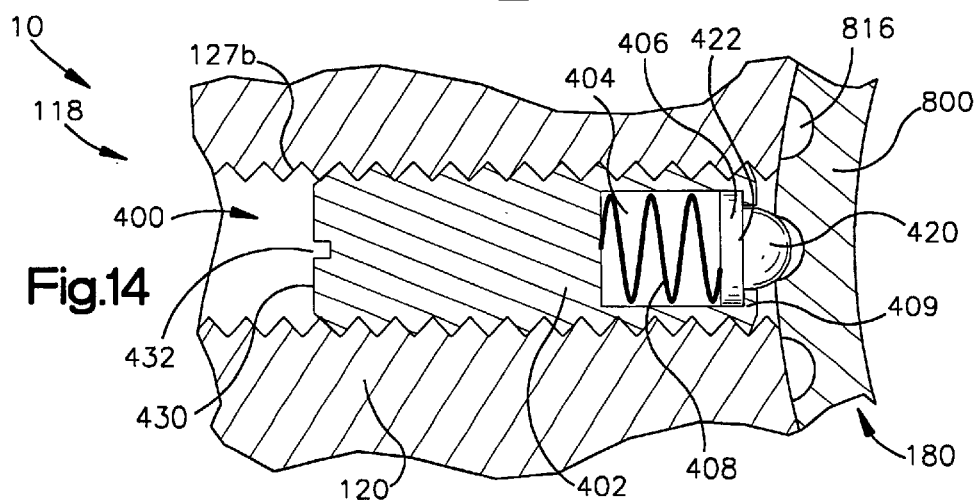
FIG. 14 is a schematic detail view of part of the apparatus in FIG. 13.

As viewed in FIG. 14, a ball plunger 400 is shown securing the base 118 to the sleeve part 800. Such a ball plunger 400 could optionally be replaced by a set screw 459. Each ball plunger 400, including those in the part 140 and base 118, has an externally threaded tubular body 402 with a cylindrical cavity 404 located therein. The cavity 404 houses a projection 406 and a coiled spring 408. The spring 408 urges each projection 406 against a lip portion 409 of the body 402. The lip portion 409 is located at one end of the cavity 404. Each ball plunger 400 has projections 406 with spherical detent members 420 and shoulder portions 422.

Each ball plunger 400 further includes a head portion 430 with a slot 432 for receiving a tool, such as a screwdriver. Each ball plunger 400 may be threadedly adjusted within a threaded bore to alter the distance that the spherical detent member 420 projects away from the threaded bore. This distance, along with the stiffness of each spring 408, will determine a holding force applied by the ball plunger 400.

As viewed in FIG. 8, the screw mechanism 160 provides for vertical adjustment of the part 140 relative to the base 118 parallel to the central axis 14 of the cannula 11. The screw mechanism 160 includes a first large diameter spindle 610, a second small diameter spindle 620, and a wheel member, or thumb wheel 630. The thumb wheel 630 and the first spindle 610 rotate about a secondary axis 614 parallel to the central axis 14 and spaced apart from the central axis. The first spindle 610 and the thumb wheel 630 may be made of plastic and integrally molded together as one piece. The right-hand threaded bore 289 of the base part 280, the first spindle 610, the second spindle 620, and the thumb wheel 630 are all symmetric about the secondary axis 614.

The first spindle 610 has right-hand male threads 611 for engaging the female threads of the right-hand threaded bore 289 of the base part 280. As the first spindle 610 is rotated, due to manual force applied to the thumb wheel 630, about the secondary axis 614, the first spindle 610 moves axially along the secondary axis 614 vertically into, or out of, the right-hand threaded bore depending upon the direction of rotation. The second spindle 620 has opposite left hand male threads 621 for engaging female threads of a left-hand threaded bore 612 centered on the secondary axis 614 and located in the first spindle 610.

The second spindle 620 further has the part 623 which is rectangular, planar end portion 623 inserted into the slot 465 of the part 140. The part 623 is a generally rectangular, planar end portion of the second spindle 620. Set screws or preferably ball plungers 400, threaded into the bores 478 in the part 140, engage planar surfaces of the end portion 623 and secure (along with the tracks 287, 288 of the base 118) the part 140 against rotational movement relative to the second spindle 620. The ball plungers 400 or set screws also releasably secure the part 140 against axial movement relative to the end portion 623 of the second spindle 620.

The end portion 623 of the second spindle 620 may have hemispherical recesses 625 for receiving the end of the set screws or the spherical detent members 420 of the ball plungers 400 (FIG. 10). The second spindle 620 may be removed from the slot 465 of the part 140 by disengaging the ends of the set screws from the hemispherical recesses 625 or by overcoming the bias of the spherical detent members 420 in the hemispherical recesses.

The thumb wheel 630 has a knurled perimeter 631 to facilitate manual rotation of the thumb wheel about the secondary axis 614. When rotation is imparted to the thumb wheel 630, the threaded engagement between the right-hand female threads of the right-hand threaded bore 289 of the base 118 and the right-hand male threads 611 of the first spindle 610 either raises or lowers the first spindle vertically relative to the base depending upon the direction of rotation. Simultaneously, the threaded engagement between the left-hand female threads of the left-hand threaded bore 612 of the first spindle 610 and the left-hand male threads 621 of the second spindle 620 either raises or lowers (depending on the direction of rotation) the second spindle vertically relative to the first spindle. This opposite hand thread arrangement results in an amplified movement of the second spindle 620 for each single rotation of the thumb wheel 630 because the two sets of threads work in concert to axially move the first spindle 610 and second spindle in the same direction, instead of acting against each other as would occur if the threads were both left-hand or both right-hand.

The part 140, being secured to the end portion 623 of the second spindle 620, is moved linearly parallel to the axis 14 of the cannula 11 (or vertically) upon rotation of the thumb wheel 630. The part 140 slides along the linear tracks 287, 288 of the guide portion 128 with the stop member 295 providing an upper limit for the position of the part 140. As the part 140 moves, the tracks 287, 288 may engage the lateral surfaces 271, 272 of the part 140 and block rotation of the part. Also, the tracks 287, 288 guide the vertical movement of the part 140. Upon vertical movement of the part 140, the endoscope 200 is vertically adjusted since it is secured in the passage in the part 140, as described above.

Figure 12:
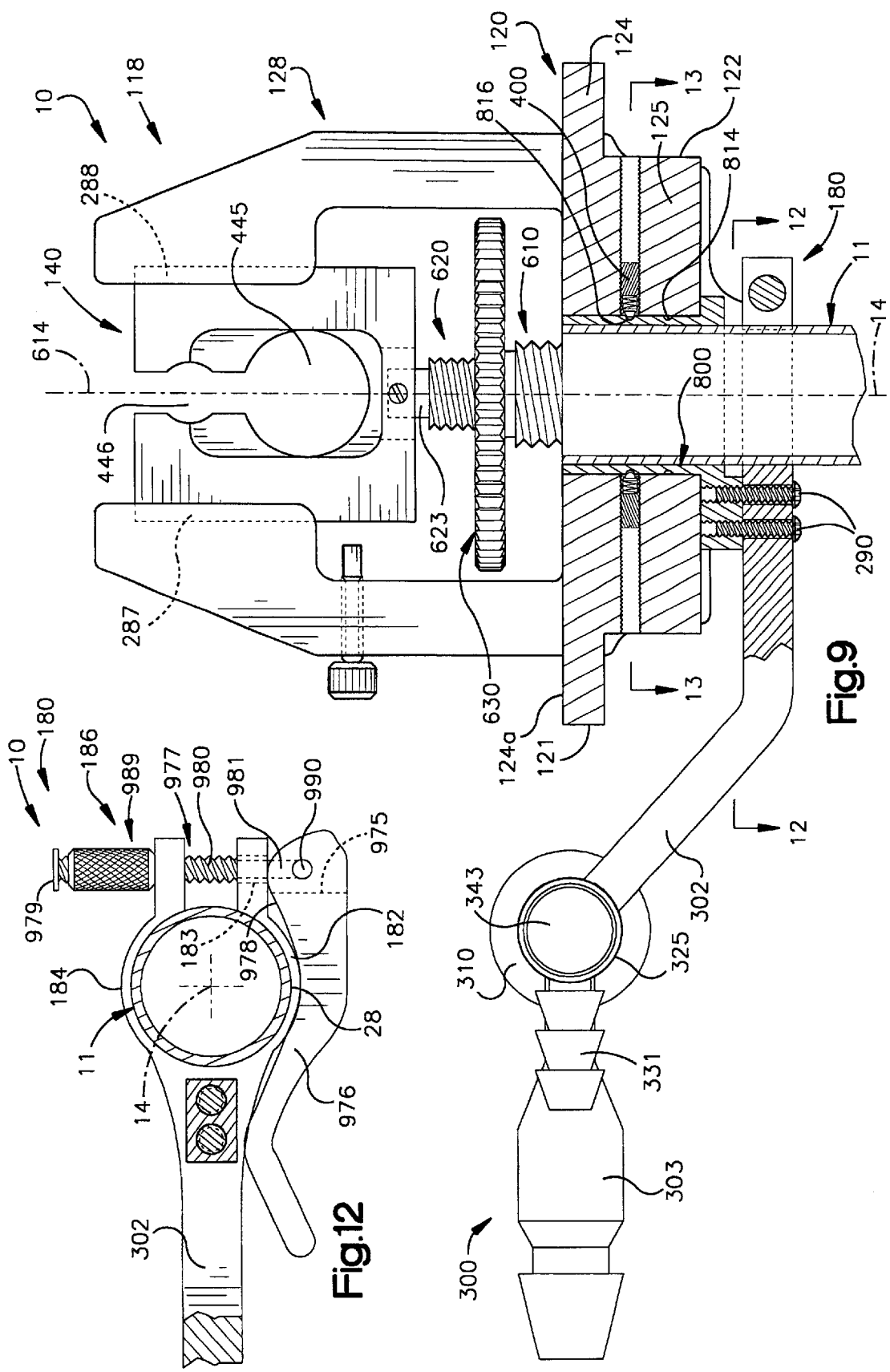
FIG. 12 is a schematic sectional view taken along line 12—12 in FIG. 9.

As viewed in FIG. 12, the cannula clamp 180 includes two gripper arms 182, 184 that are deflected toward each other to clamp against the outer surface 28 of the cannula 11, a gripper actuating lever 976 for deflecting the gripper arms 182, 184 into gripping engagement with the outer surface 28 of the cannula, and an adjustment mechanism 186 for changing the relative position of the gripper arms 182, 184 from which the arms are moved by the actuating lever to enable the arms to clamp different diameter cannulas. The gripper actuating lever 976 also releases the gripper arms 182, 184 from gripping engagement with the outer surface 28 of the cannula 11. When released, the gripper arms will spring away from the outer surface 28 of the cannula 11. The two gripper arms 182, 184 may grip the plastic tubing 32 depending on the position of the plastic tubing on the first tubular portion 20 of the cannula 11 (as described above). References in this application to gripping the outer surface of the cannula are meant to also cover the gripper arms engaging the plastic tubing.

The adjustment mechanism 186 includes a threaded stud 977 with a longitudinal axis, an adjustment knob 989 with a female threaded bore, and a lock pin 990. The threaded stud 977 has a head 979, a threaded shaft 980 for screwing into, and through, the threaded bore of the adjustment knob 989, and an oblong, or flat end 981 which extends through an oblong bore 183 in the gripper arm 182. Alternative structures for the adjustment mechanism 186 are envisioned by the present invention.

During assembly, the flat end 981 of the threaded stud 977 is threaded through the bore of the adjustment knob 989 and inserted horizontally through a circular bore (not shown) in the gripper arm 184 that is larger in diameter than the diameter of the threaded stud 977 and through the oblong bore 183 in the gripper arm 182. The flat end 981 of the threaded stud 977 is then horizontally inserted into a longitudinal slot 975 in the lever 976. The threaded stud 977 is secured against rotation relative to gripper arms 182, 184 by engaging surfaces of the gripper arms 182, 184 defining bore 183 on gripper arm 182 and similar surfaces on arm 184 defining the oblong bore in arm 184. The lock pin 990 is then inserted vertically through a bore (not shown) in the lever 976 and through a bore (not shown) in the flat end 981 of the threaded stud 977 thereby securing the adjustment mechanism 186 together. The lever 976 is free to rotate about the lock pin 990.

The adjustment knob 989 may be axially positioned along the threaded stud 977 by rotation of the adjustment knob about the secured threaded stud. By changing the axial position of the adjustment knob 989, the gripper arm 184 moves relative to the threaded stud 977 and the distance between the gripper arms 182, 184 changes and the relative positions of the gripper arms change. Rotation of the adjustment knob 989 in one direction may move the gripper arms 182, 184 closer together and rotation in the opposite direction may allow the arms to spring apart.

A camming surface 978 on the lever 976, adjacent the gripper arm 182, moves the arms 182, 184 a predetermined distance together to grip the outer surface 28 of the cannula 11 as the lever 976 is rotated clockwise about the lock pin 990 to the position shown in FIG. 12. Counterclockwise rotation of the lever 976 about the lock pin 990, from the position shown in FIG. 12, allows the gripper arms 182, 184 to spring (move) apart and releases the outer surface 28 of the cannula 11 from the cannula clamp 180.

The gripper arms 182, 184 have a normal position from which the gripper arms may be moved a predetermined distance by the actuating lever 976 to grip a cannula 11 having a first diameter. Rotation of the adjustment knob 989 in one direction relative to the stud 977 causes arms 182, 184 to resiliently deflect toward each other and take new positions. The gripper arms 182, 184 may be moved from these new positions a predetermined distance by the actuating lever 976 to grip a cannula 11 having a second diameter smaller than the first diameter. Rotation of the adjustment knob 989 in a second direction opposite the first direction allows the gripper arms 182, 184 to spring back toward their normal positions. It should be apparent that the adjustment knob 989 enables the cannula clamp 180 to securely grip cannulas of different diameters.

When the cannula clamp 180 is released from the cannula 11, the base 118 and parts (i.e., the endoscope) attached to the base may move along the central axis 14 of the cannula 11 relative to the cannula. After the apparatus 10 is initially aligned with the cannula 11, the endoscope 200 may be positioned on the apparatus 10 and axially adjusted along the central axis 14 in this manner. After the cannula clamp 180 grips the outer surface 28 of the cannula 11, the screw mechanism 160 provides for vertical adjustment of the endoscope 200 relative to the cannula.

As viewed in FIG. 6, the cylindrical sleeve part 800, which is secured to the cannula clamp 180, may be inserted into the central aperture 126 of the base 118. The sleeve part 800 has a passage extending through the sleeve part, which passage receives the cannula 11. As viewed in FIG. 9, the upper edges of the sleeve part 800 and the proximal end 22 of the cannula 11 are typically assembled flush with the upper surface area 124a of the first disk 124. The sleeve part 800 is centered about the central axis 14 and includes a cylindrical outer surface 810, a horizontal groove 814 which extends around the cylindrical outer surface, and a horizontal array of spaced apart recesses 816 in the cylindrical outer surface. The recesses 816 lie in a horizontal plane parallel to, and axially offset from, a plane defined by the groove 814, both planes being perpendicular to the central axis 14.

As viewed in FIG. 13, the sleeve part 800 is axially secured in the central aperture 126 of the base 118 by set screws 459 or, more preferably, by ball plungers 400 extending radially into the central aperture and engaging the groove 814. The sleeve part 800 is rotationally (and axially) secured in the central aperture 126 of the base 118 by the set screws 459 or the ball plungers 400 extending radially into the central aperture and being received in the recesses 816. The set screws 459 or ball plungers 400 are threaded radially inward through threaded radial bores 127 that penetrate radially inward from the second perimeter 122 of the base 118 to the central aperture 126. Four radial bores 127a are axially aligned with the groove 814 and are located at 90° increments about the central aperture 126. Correspondingly, four additional radial bores 127b are axially aligned with the recesses 816 at 90° increments, but angularly offset 45° from the four bores 127a.

If set screws 459 are used, the distal ends of the set screws form detents that engage the groove 814 and support the sleeve part 800 in the central aperture 126, but allow the base 118 and sleeve part to rotate relatively about the central axis 14. The recesses 816 of the sleeve part 800 and the detents formed by set screws 459 form an indexing mechanism that secures the sleeve part at selected angular increments about the central axis 14 relative to the base 118. Thirty-six (36) recesses 816 are, spaced about the cylindrical outer surface 810 at 10' increments. Thus, when the set screws 459 are threadedly disengaged from the recesses 816, the base 118 may be rotated about the central axis 14 relative to the fixed cannula clamp 180, while the base 118 is axially secured by the set screws 459 engaging the groove 814. After 10° of rotation (or some multiple of 10°), the set screws 459 may be threaded inward for reengaging the recesses 816 and rotationally securing the base 118 to the cannula clamp 180. An access bore 129 is located in the base part 280 for providing access to the bore 127b that is disposed against the guide portion 128 of the base 118.

If ball plungers 400 are used, which is preferable, the spherical detent members 420 form detents that engage in the groove 814 and support the sleeve part 800 in the central aperture 126, but allow the base 118 and the sleeve part to rotate about the central axis 14. The recesses 816 of the sleeve part 800 and the detents formed by ball plungers 400 form an indexing mechanism that secures the sleeve part at selected angular increments about the central axis 14 relative to the base 118. Thirty-six (36) recesses 816 are spaced about the cylindrical outer surface 810 at 10° increments. Thus, with minimal manual force to overcome the biasing force of the ball plungers 400, the base 118 may be rotated about the central axis 14 relative to the fixed cannula clamp 180, thereby disengaging the biased spherical detent members 420 from the recesses 816. The base 118 will remain axially secured by the ball plungers 400 engaging the groove 814. The spherical detent members 420 reengage the recesses after 10° of rotation.

However, if rotation of the base 118 more than 10° is desired, the manual force applied to the base can continue to rotate the base. As should be apparent, the base 118 and the endoscope 200 may rotate about 270° about the central axis 14 of the cannula 11 and be adjustably fixed at 10° increments. This enables the surgeon to view different parts of the surgical site, as desired.

Figure 18:
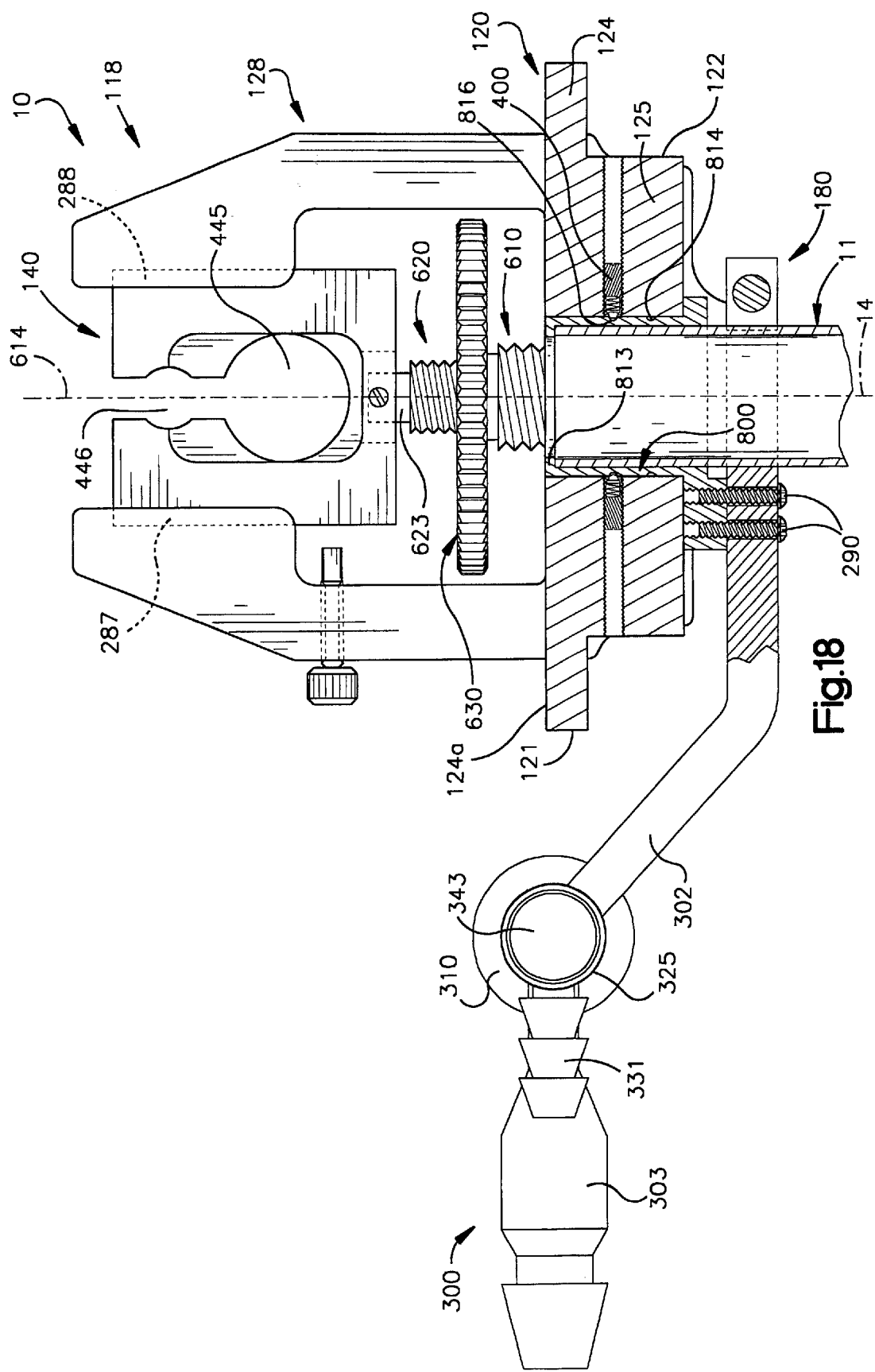
FIG. 18 is a schematic sectional view similar to FIG. 9 showing another feature of the apparatus of FIG. 6.

The sleeve part 800 of the cannula clamp 180 can be easily removed from the central aperture 126 for cleaning, maintenance, etc. of the parts by disengaging the set screws 459 from the groove 814 and the recesses 816, or by overcoming the biasing force applied by the ball plungers 400 to the sleeve part. As viewed in FIG. 18, the sleeve part 800 may have an annular retaining lip 813 for engaging the proximal end 22 of the cannula 11. The retaining lip 813 extends radially inward and provides an upper limit stop that prevents the cannula 11 from extending upward (axially) from the central aperture 126. The upper edge of the retaining lip 813 is typically mounted flush with the upper surface area 124a of the first disk 124.

As viewed in FIGS. 15–17, the cannula clamp 180 is a part of the support arm 300 for attaching the apparatus 10 to a mechanical robotic arm 301. The support arm 300 includes an arm portion 302 which may be formed integrally with the gripper arms 182, 184. As viewed in FIG. 9, the arm portion 302 extends upwardly away from the gripper arms 182, 184 in order to minimize the possibility of contact with the patient during surgery.

The support arm 300 also includes an arm portion 303. The arm portion 303 has an attaching structure 304, including a groove 305, which snaps into a socket in the mechanical arm 301. Detents of any suitable type and designated 306 in the mechanical arm 301, hold the arm portion 303 in position in the socket in the mechanical arm 301. The detents 306 may be controlled by external actuation levers (not shown) on the mechanical arm 301 for manually releasing the arm portion 303 from the mechanical arm 301.

The arm portions 302 and 303 are pivotally connected to each other by a fastener 310. The fastener 310 extends through an opening 311 in the arm portion 302 and threads into a threaded opening 312 in the arm portion 303. When the fastener 310 is released, the arm portions 302, 303 may pivot relative each other about a pivot axis 314. The pivot axis 314 is centered on the axis of the fastener 310 and the axis of the threaded opening 312. When the fastener 310 is tightly screwed into the threaded opening 312, the arm portions 302, 303 are secured together against pivoting movement. When the fastener 310 is released, the arm portions 303, 302 may pivot relative to each other about the axis 314.

The end of the arm portion 302, which is adjacent to the arm portion 303, has a convex surface 350, which is curved about the axis 314. The arm portion 303 has a concave surface 351, which is also curved about the axis 314. The surfaces 350, 351 move concentrically relative to each other when the arm portions 302, 303 pivot relatively about the axis 314.

The arm portion 303 has a set of teeth 320 which encircle the axis 314 and which project axially toward a set of teeth 321 on the arm portion 302. The teeth 321 project axially toward the teeth 320. The teeth 320 and the teeth 321 mesh with each other and provide a locking action so that the arm portions 302, 303 are positively locked against relative movement about the axis 314 when the fastener 310 is tightly screwed into the opening 312. The teeth 320, 321 define a lock which blocks relative rotation of the arm portions 302, 303 about the axis 314. When the fastener 310 is loosened, the arm portions 302, 303 may be rotated relative to each other about the axis 314, and thus, the arm portions 302, 303 may pivot relative to each other to adjust the position of the apparatus 10.

A cylindrical projection 325 is welded to the arm portion 303. Thus, the projection 325 and arm portion 303 are fixedly connected together. The projection 325 is centered on the axis 314 and contains a chamber 328.

As viewed in FIG. 17, the chamber 328 communicates with a fluid passage 329 in a male fluid connector 331. The male connector 331 attaches to a male connector 333 on the mechanical arm 301 by means of a flexible hose 392 so that the fluid passage 329 communicates with a fluid passage in the mechanical arm 301.

As viewed in FIG. 15, the chamber 328 is closed at its upper end by a cap 335. The cap 335 has an opening 336 centered on the axis 314. The opening 336 communicates with the chamber 328. A manually movable internal valve member 340 normally closes the opening and blocks the chamber 328 from communicating with the ambient air surrounding the support arm 300. The valve member 340 is connected to a stem 341, which is also centered on the axis 314. The stem 341 has a knob or button 343 on its end which may be manually depressed to move the stem 341 and valve member 340 downward into the chamber 328. When the stem 341 and valve member 340 are so moved, the chamber 328 is in communication with the ambient air surrounding the device due to the unblocking of the opening 336.

The mechanical arm 301 is a known device and is of the type generally disclosed in U.S. Pat. No. 4,863,133. The mechanical arm 301 is sold by Leonard Medical, Inc. 1464 Holcomb Road, Huntington Valley, Pa., 19006. The mechanical arm 301 includes relatively movable parts, which permit movement and adjustment of the apparatus 10 in a variety in planes, directions, and orientations. The mechanical arm 301 permits easy movement when a vacuum is not applied to the arm 301. When a vacuum is applied to the arm 301, relative movement of the parts of the arm 301 is resisted, and therefore adjustment of the apparatus 10 is difficult.

When the button 343 is depressed, the chamber 328 loses its vacuum and the pressure in the chamber 328 increases toward ambient pressure. The passage 329 communicates this pressure increase to the mechanical arm 301, and thus the parts of the mechanical arm 301 are free to move and allow for adjustment of the position of the apparatus 10 by the surgeon.

Accordingly, when the surgeon uses the apparatus 10, the support arm 300 is snapped into the socket of the mechanical arm 301 where it is held by the detent 306. The surgeon may then depress the button 343 and relatively move parts of the mechanical arm 301 as well as the apparatus 10 into the position where the surgeon desires the apparatus 10 to be. This position may be where the central aperture 126 of the base 118 and the sleeve portion 800 are aligned with the proximal end 22 of the cannula 11 and the distal end 24 of the cannula 11 is located in an incision in the body of a patient. The endoscope 200 may be mounted on the apparatus 10, and the surgeon may make adjustments prior to, and during, the surgical procedure as desired, as described above.

As viewed in FIG. 9, the fixed connection of the sleeve portion 800 to the support arm 300 may be made by one or more suitable metal fasteners 290, such as rivets or bolts. The sleeve portion 800 is axially offset from the gripper arms 182, 184 in order to allow the gripper arms to flex against the outer surface 28 of the cannula 11.

The entire apparatus 10 can be constructed from metal or any other suitable material having sufficient mechanical strength, flexibility, and durability. Certain parts may be made from materials permitting X-rays and other techniques for viewing the surgical site (i.e., radiopaque parts). Other parts may also be made from non-magnetic materials to reduce electromagnetic interference (i.e., electromagnetic insulating parts).

From the above description of the invention, those skilled in the art will perceive improvements, changes and modifications. Such improvements, changes and modifications within the skill of the art are intended to be covered by the appended claims.

Having described the invention, the following is claimed:

1. An apparatus for supporting an endoscope for viewing a surgical site in a patient during surgery on the patient, said apparatus comprising:
   a base having a guide portion;
   a part adapted to be fixed to the endoscope, said part engaging said guide portion and being movable relative to said guide portion; and
   a screw mechanism connected between said base and said part, at least a portion of said screw mechanism being rotatable to slide said part relative to said guide portion to change a position of the endoscope relative to the patient.

2. The apparatus as defined in claim 1 further including a thumb wheel for rotating said portion of said screw mechanism to change the position of said part relative to said guide portion.

3. The apparatus as defined in claim 2 wherein said screw mechanism comprises a first threaded spindle rotatably screwed into first threads on said base, and a second threaded spindle fixed against rotation relative to said guide portion, said second threaded spindle being rotatably screwed into second threads on said first spindle, said thumb wheel rotating said first threaded spindle.

4. The apparatus as defined in claim 3 wherein said first threads and said second threads are of opposite hand.

5. The apparatus as defined in claim 1 wherein said part engages a track on said guide portion, said track allowing linear movement of said part relative to said base.

6. The apparatus as defined in claim 1 wherein said base further includes a base portion with a central aperture for receiving an end portion of a cannula.

7. The apparatus as defined in claim 1 further including a cannula clamp associated with said base and a connection between said base and said cannula clamp, said connection enabling said base to rotate relative to said cannula clamp about an axis of a cannula.

8. The apparatus as defined in claim 7 wherein said connection includes an index mechanism for retaining said base at incremental angular positions about the axis of the cannula.

9. The apparatus as defined in claim 8 wherein said index mechanism includes a sleeve part, said sleeve part being disposed symmetrically about the axis of the cannula.

10. The apparatus as defined in claim 9 wherein said sleeve part includes a series of angularly spaced apart recesses and said base includes spaced apart members for receipt in said recesses for fixing the angular position of said base relative to the cannula.

11. An apparatus for supporting an endoscope for viewing a surgical site in a patient during surgery on the patient, the endoscope extending through a cannula into the patient, said apparatus comprising:
    a base;
    a support mechanism for supporting the endoscope on said base;
    a cannula clamp for clamping against an outer surface of the cannula; and
    a connection between said base and said cannula clamp, said connection enabling said base to rotate relative to said cannula clamp about an axis of the cannula, said connection including an index mechanism with parts interposed between said base and said cannula clamp for retaining said base at incremental relatively rotated positions relative to said cannula clamp.

12. The apparatus as defined in claim 11 wherein said parts of said index mechanism include a first part connected with one of said base and cannula clamp, said first part having a series of angularly spaced apart recesses, said parts of said index mechanism further including a second part connected with the other of said base and cannula clamp, said second part being received by said recesses.

13. The apparatus as defined in claim 12 wherein said base has a central aperture and said cannula clamp has a sleeve part secured thereto, said sleeve part being received in said central aperture, said sleeve part having said recesses, said base including spring biased detents on said base for receipt in said recesses.

14. The apparatus as defined in claim 13 wherein said sleeve part has a passage therethrough for receiving the cannula.

15. The apparatus as defined in claim 11 further including a part adapted to be fixed to the endoscope, said base including a guide portion, said part engaging said guide portion and being movable relative to said guide portion.

16. The apparatus as defined in claim 15 further including a screw mechanism connected between said base and said part, said screw mechanism being rotatable to slide said part relative to said guide portion.

17. The apparatus as defined in claim 15 wherein said guide portion includes two spaced apart upright members extending parallel to each other.

18. The apparatus as defined in claim 16 wherein said screw mechanism includes a first spindle with right-hand male threads and a second spindle with left-hand male threads.

19. The apparatus as defined in claim 11 wherein said cannula clamp includes an adjustment mechanism for allowing said cannula clamp to attach to cannulas of different sizes.

20. The apparatus as defined in claim 11 further including an actuating lever for actuating said cannula clamp to clamp against a cannula.

21. An apparatus for supporting an endoscope for viewing a surgical site in a patient during surgery on the patient, the endoscope extending through a cannula into the patient, said apparatus comprising:

a base for supporting the endoscope;

a cannula clamp including a pair of spaced apart arms for clamping against an outer surface of the cannula through which the endoscope extends; and an actuator for moving said arms a predetermined distance toward each other to effect clamping against a cannula;

said cannula clamp further including an adjustment mechanism for changing the relative position of said arms from which said arms are moved by said actuator to enable said arms to clamp different diameter cannulas.

22. The apparatus as defined in claim 21 wherein said adjustment mechanism comprises a threaded member extending through openings in said arms, said arms being movable relative to said threaded member and a knob threaded on said threaded member and which on rotation moves axially on said threaded member to change the relative positions of said arms.

23. The apparatus as defined in claim 21 further including a part adapted to be fixed to the endoscope, said base including a guide portion, said guide portion engaging said part and allowing vertical movement of said part relative to said guide portion.

24. The apparatus as defined in claim 23 further including a screw mechanism connected between said base and said part.

25. The apparatus as defined in claim 24 wherein said screw mechanism is rotatable to slide said part relative to said guide portion.

26. The apparatus as defined in claim 24 further including a thumb wheel for rotating a portion of said screw mechanism.

27. The apparatus as defined in claim 23 wherein said guide portion includes a linear track for preventing rotation of said part relative to said base.

28. The apparatus as defined in claim 23 further including a screw mechanism for imparting vertical linear movement to the endoscope relative to a cannula.

29. The apparatus as defined in claim 21 further including an index mechanism for retaining said base at incremental relatively rotated positions relative to said cannula clamp.

30. The apparatus as defined in claim 21 wherein said cannula clamp is adapted to rotate and move linearly relative to the endoscope.

31. An apparatus for supporting an endoscope for viewing a surgical site in a patient during surgery on the patient, said apparatus comprising:

a part for engaging the endoscope, said part having a first surface portion for engaging opposed sides of the endoscope and a second surface portion spaced apart from said first surface portion for engaging a part of the endoscope defining a light port.

32. The apparatus as defined in claim 31 further including a base for supporting said part for axial movement of said part relative to an axis of a cannula.

33. The apparatus as defined in claim 32 wherein said base has a guide portion for guiding axial movement of said part and preventing rotation of said part relative to a cannula.

34. The apparatus as defined in claim 31 further including a cannula clamp associated with said base for clamping against an outer surface of a cannula.

35. The apparatus as defined in claim 34 wherein said cannula clamp includes two arms, and further including an adjustment mechanism for enabling said arms to clamp different diameter cannulas.

36. The apparatus as defined in claim 32 further including a screw mechanism associated with said base for axially moving said part to adjust the position of an endoscope relative to an axis of a cannula.

37. The apparatus as defined in claim 36 wherein said part includes a slot for receiving said screw mechanism and further including a threaded member connecting said part and said screw mechanism in said slot.

38. The apparatus as defined in claim 31 further including an index mechanism associated with said base for enabling incremental rotational adjustment of the position of said base and the endoscope relative to a cannula.

39. The apparatus as defined in claim 31 further including a base associated with said part and a mechanism for adjusting the position of the part and the endoscope relative to said base.

40. The apparatus as defined in claim 39 wherein said mechanism includes a sleeve for engaging an end of a cannula, said sleeve having an axis, said base and said sleeve being relatively rotatable about said axis of said sleeve.

41. An apparatus for supporting an endoscope for viewing a surgical site in a patient during surgery on the patient, said apparatus comprising:

a base for supporting the endoscope;

a first part adapted to be fixed to the endoscope;

a second part adapted to be fixed to a cannula with a longitudinal axis; and a mechanism for axially and rotationally adjusting said first part relative to said second part, said mechanism including a member supported on said base for rotation on said base about an axis parallel to the longitudinal axis of the cannula and spaced from the longitudinal axis of the cannula.

42. An apparatus for supporting an endoscope for viewing a surgical site in a patient during surgery on the patient, said apparatus comprising:

a cannula for insertion into a patient, said cannula having a longitudinal axis;

a cannula clamp for adjustably engaging an outer surface of said cannula;

a base supported for rotation relative to said cannula clamp about a longitudinal axis of said cannula; and a part adapted to be fixed to an endoscope, said part being supported for linear movement on said base, the movement of said part being parallel to said longitudinal axis of said cannula.

* * * * *